(12) United States Patent
Yoshioka et al.

(10) Patent No.: US 9,198,808 B2
(45) Date of Patent: Dec. 1, 2015

(54) ABSORBENT ARTICLE

(75) Inventors: Toshiyasu Yoshioka, Kanonji (JP); Shunsuke Masaki, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 228 days.

(21) Appl. No.: 13/824,374

(22) PCT Filed: Sep. 26, 2011

(86) PCT No.: PCT/JP2011/072705
§ 371 (c)(1),
(2), (4) Date: Mar. 17, 2013

(87) PCT Pub. No.: WO2012/043844
PCT Pub. Date: Apr. 5, 2012

(65) Prior Publication Data
US 2013/0190710 A1  Jul. 25, 2013

(30) Foreign Application Priority Data

Sep. 30, 2010  (JP) .................................. 2010-223096

(51) Int. Cl.
*A61F 13/15* (2006.01)
*A61F 13/511* (2006.01)
(Continued)

(52) U.S. Cl.
CPC ......... *A61F 13/51108* (2013.01); *A61F 13/515* (2013.01); *A61F 13/5116* (2013.01);
(Continued)

(58) Field of Classification Search
CPC . A61F 13/511; A61F 13/5116; A61F 13/513; A61F 13/51104; A61F 13/515; A61F 2013/51178; A61F 2013/51182; A61F 2013/51355; A61F 2013/530379; A61F 2013/53086; A61F 2013/53043; A61F 2013/530489; A61F 2013/530598; A61F 2013/51191; A61F 2013/51078; A61F 2013/51108; A61F 2013/51083; A61F 2013/51085; A61F 2013/51088

USPC ......................................... 604/367, 368, 378
See application file for complete search history.

(56) References Cited

U.S. PATENT DOCUMENTS 5,458,592 A   10/1995  Abuto et al.
6,102,892 A *  8/2000  Putzer et al. ............. 604/385.01
(Continued)

FOREIGN PATENT DOCUMENTS

EP   1064893 A2   1/2001
EP   2087871 A1   8/2009
(Continued)

OTHER PUBLICATIONS

Supplementary European Search Report dated Jun. 18, 2014, corresponds to European patent application No. 11829397.
(Continued)

*Primary Examiner* — Lynne Anderson
(74) *Attorney, Agent, or Firm* — Hauptman Ham, LLP (57) ABSTRACT

An interior body of a disposable diaper includes a liquid-permeable front sheet, a liquid-impermeable back sheet and a liquid-retaining absorbent core. The front sheet has a single sheet including spunbond layers on the front side and back side and a melt blown layer between the spunbond layers. The absorbent core has fiber aggregates and super-absorbent polymer particles. The front sheet is directly bonded to the skin side surface of the absorbent core. The length of the front sheet is longer than the length of the absorbent core, so that the front sheet has extended sections which extend outward in the lengthwise direction from both ends of the absorbent core in the lengthwise direction, while the extended sections are each continuously connected in the transverse direction with the front sheet or back sheet which overlaps with the extended section. The extended sections can directly contact the skin of the wearer.

11 Claims, 10 Drawing Sheets

(51) Int. Cl.
*A61F 13/513* (2006.01)
*A61F 13/515* (2006.01)
*A61F 13/51* (2006.01)
*A61F 13/53* (2006.01)
*A61F 13/49* (2006.01)

(52) U.S. Cl.
CPC ..... *A61F13/51104* (2013.01); *A61F 13/51121* (2013.01); *A61F 13/51394* (2013.01); *A61F 13/49061* (2013.01); *A61F 2013/51078* (2013.01); *A61F 2013/51178* (2013.01); *A61F 2013/51182* (2013.01); *A61F 2013/530598* (2013.01)

(56) References Cited

U.S. PATENT DOCUMENTS

| | | | |
|---|---|---|---|
| 2005/0033255 A1* | 2/2005 | Fossum et al. | 604/370 |
| 2006/0069368 A1* | 3/2006 | Van Himbergen et al. | 604/378 |
| 2008/0021426 A1* | 1/2008 | Nakagawa et al. | 604/378 |
| 2008/0286320 A1* | 11/2008 | Vega et al. | 424/402 |
| 2010/0217216 A1 | 8/2010 | Sue et al. | |
| 2011/0118690 A1* | 5/2011 | Oku et al. | 604/385.16 |

FOREIGN PATENT DOCUMENTS

| | | | |
|---|---|---|---|
| JP | 9164164 A | 6/1997 | |
| JP | 2002119539 A | 4/2002 | |
| JP | 3594099 B2 | 11/2004 | |
| JP | 20057188 A | 1/2005 | |
| JP | 2008178682 A | 8/2008 | |
| JP | 2009106666 A | 5/2009 | |
| JP | 2009178384 A | 8/2009 | |
| JP | 4526323 B2 | 8/2010 | |
| WO | 2007032710 A1 | 3/2007 | |
| WO | 2008067184 A2 | 6/2008 | |

OTHER PUBLICATIONS

International Search Report for PCT/JP2011/072705 dated Nov. 15, 2011.

Office Action mailed Mar. 13, 2014, corresponds to Chinese patent application No. 201180047441.1.

* cited by examiner

ABSORBENT ARTICLE

RELATED APPLICATIONS

The present application is a National Phase of International Application Number PCT/JP2011/072705, filed Sep. 26, 2011, and claims priority from Japanese Application Number 2010-223096, filed Sep. 30, 2010.

TECHNICAL FIELD

The present invention (disclosure) relates to an absorbent article.

BACKGROUND ART

In the prior art there are known absorbent articles, such as disposable diapers, that comprise a liquid-permeable front sheet, a liquid-impermeable back sheet, a liquid-retaining absorbent core and a core wrap surrounding the absorbent core (see PTL 1).

CITATION LIST

Patent Literature

PTL 1: U.S. Pat. No. 5,458,592

SUMMARY OF INVENTION

Technical Problem

Incidentally, the number of disposable diapers in use in developing countries is still low compared to developed countries. This is believed due to the high cost of diapers for people living in developing countries. For provision of diapers at low cost, therefore, it is necessary to significantly reduce the production cost of diapers.

Significant reduction in production cost will require a major change, for example, in construction to eliminate parts commonly provided in diapers for advanced countries. However, a construction which reduces a production cost significantly is not disclosed in PTL 1.

Solution to Problem

According to the present invention there is provided an absorbent article comprising a liquid-permeable front sheet, a liquid-impermeable back sheet and a liquid-retaining absorbent core, wherein the front sheet consists of a single sheet comprising spunbond layers on the front side and back side and a melt blown layer between the spunbond layers, the absorbent core consists of fiber aggregates and super-absorbent polymer particles, the front sheet covers the skin side surface of the absorbent core while being directly bonded to the skin side surface, the length of the front sheet in the lengthwise direction is longer than the length of the absorbent core in the lengthwise direction so that the front sheet is provided with extended sections which extend outward in the lengthwise direction from both ends in the lengthwise direction of the absorbent core, the extended sections being each continuously connected (joined together) in the transverse direction with the front sheet or back sheet which overlaps with the extended section, and the extended sections can be contacted with the skin of a wearer.

Advantageous Effects of the Invention

It is possible to greatly reduce production cost of absorbent articles without significantly reducing function.

DESCRIPTION OF EMBODIMENTS

The inventor(s) has/have recognized that significant reduction in production cost is possible when one or more parts commonly provided in diapers for developed countries is/are eliminated. If, for example, the front sheet is arranged to perform the added function of surrounding the absorption core, this would allow the core wrap to be eliminated, thereby allowing production cost to be greatly reduced without notably reducing functionality.

The present invention may be applied to a disposable diaper comprising an interior body and an exterior body (also referred to as chassis or outer cover). Alternatively, the present invention may also be applied to other absorbent (absorptive) articles such as sanitary napkins, panty liners and incontinence pads.

Figure 1:
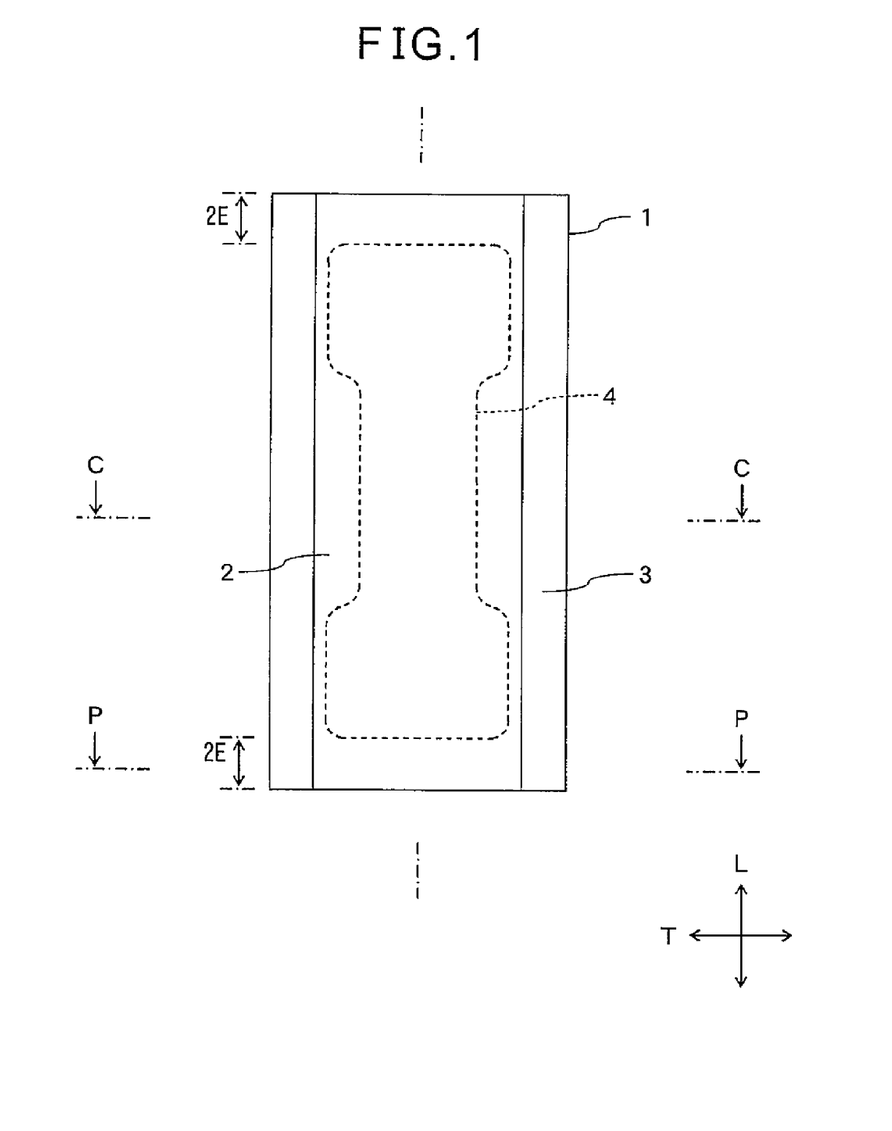
FIG. 1 is a plan view of an interior body, in accordance with a first embodiment of the present invention.
Figure 2:
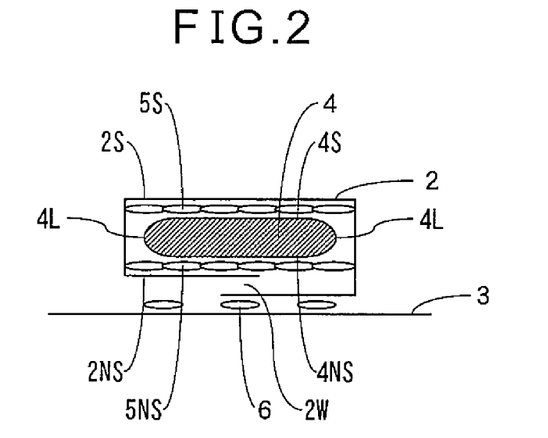
FIG. 2 is a schematic cross-sectional view of FIG. 1 along line C-C.
Figure 3:
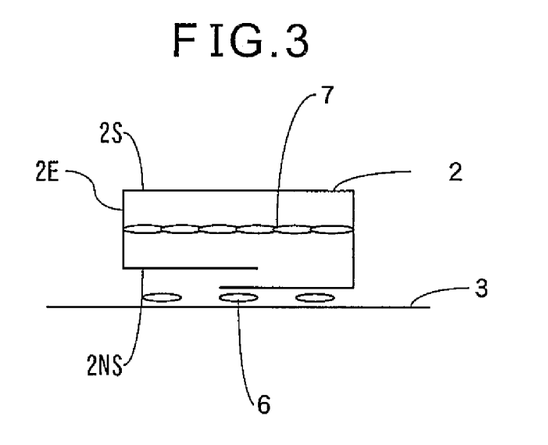
FIG. 3 is a schematic cross-sectional view of FIG. 1 along line P-P.

Referring to FIG. 1, FIG. 2 and FIG. 3, the interior body 1 of the disposable diaper in accordance with a first embodiment comprises a liquid-permeable front sheet 2, a liquid-impermeable back sheet 3 and a liquid-retaining absorbent (absorptive) core 4. In FIG. 1, L indicates the lengthwise direction of the interior body 1, and T indicates the transverse direction perpendicular to the lengthwise direction.

The front sheet 2 consists of a single sheet, preferably in a rectangular shape, and may comprise, for example, spunbond layers on the front side (also referred to as skin side) and back side (also referred to as non-skin side), and a melt blown layer between the spunbond layers. In a preferred case, the basis weight of the entire front sheet 2 may be about, for example, 10 g/m², the basis weight of both the spunbond layers may be about, for example, 8 g/m² and the basis weight of the melt blown layer may be about, for example, 2 g/m². The melt blown layer may also be coated with a hydrophilic lubricant.

The single sheet of the front sheet 2 may be a laminated sheet formed by stacking the front side and back side spunbond layers with the melt blown layer in between, and then pattern embossing the front side spunbond layer while flat embossing the back side spunbond layer. In the pattern embossing and flat embossing, the fibers inside the front sheet 2 are contact bonded while being heated. The pattern embossing is carried out using an embossing tool having a patterned indented surface, while the flat embossing is carried out using an embossing tool having a flat surface.

The two spunbond layers of the front sheet 2 preferably have a fiber orientation in the lengthwise direction. The fiber orientation of the sheet can be determined based on the tensile strength of the sheet, for example. That is, samples are prepared along the lengthwise direction and the transverse direction of the sheet, and the tensile strength under constant stretching is measured using a tensile tester (Shimadzu Corp., Autograph). When the tensile strength of the sample along the lengthwise direction is larger than the tensile strength of the sample along the transverse direction, the fiber orientation is judged to be along the lengthwise direction.

The front sheet 2 preferably has a liquid diffusibility of, for example, at least 20 mm based on a Klemm water absorption test (JIS-L1907, P8141).

The Klemm water absorption test can be carried out in the following manner. Specifically, a sample having a width of 15 mm and a length of 100 mm is prepared, and is suspended vertically using a suspender. The lower end part of the sample having a 15 mm length is then immersed in the distilled water, and is kept there for 10 minutes. After that, the height of water ascending through the sample by capillary action is measured. The test is carried out at a temperature of 20±1° C.

In addition, the tensile strength in the lengthwise direction and the tensile strength in the transverse direction of the front sheet 2 are each preferably at least 4.0 N/25 mm, both when dry and when wet. It is confirmed that such tensile strengths prevent the front sheet from being torn when the load is applied to the front sheet due to the movement of the wearer.

The tensile strength (N/25 mm) can be measured in the following manner. Specifically, a test sample having a width of 25 mm and a length of 50 mm is prepared. In more detail, when measuring the tensile strength in the lengthwise direction, the sample is prepared so that the lengthwise direction of the sample extends in the lengthwise direction of the diaper. When measuring the tensile strength in the width direction, the sample is prepared so that the lengthwise direction of the sample extends in the width direction of the diaper. The tensile strength of the sample is then measured using a tensile tester (Shimadzu Corp., Type AG-50NI). That is, the sample is stretched by 100 mm/min until the sample is broken. The maximum strength of the sample during the measurement is determined as the tensile strength of the sample.

The tensile strength of the sample when dry is measured using a dry sample. The tensile strength of the sample when wet is measured using a wet sample. The wet sample is obtained by putting drops of distilled water onto the sample until the distilled water penetrates the entire sample.

The back sheet 3 preferably has a rectangular shape, and is composed of, for example, a hydrophobic nonwoven fabric, an impermeable plastic film, or a laminated sheet comprising a nonwoven fabric and an impermeable plastic film. The back sheet 3 may be either air permeable or non-air permeable.

The absorbent core 4 preferably comprises broad sections at both ends in the lengthwise direction, and a narrow section in the middle between the broad sections, and consists of fiber aggregates and super-absorbent polymer particles. The fiber aggregates may comprise, for example, cellulose-based fibers such as pulp fiber, cotton fiber or rayon fiber, or synthetic fiber composed of a polyester/polyethylene-based synthetic resin. The super-absorbent polymer (SAP) particles may comprise, for example, an acrylic acid-based polymer or copolymer that gels by retention of liquid, and are preferably capable of absorbing and retaining liquid in an amount of over 15 times their own weight.

The weight ratio of the SAP particles in the absorbent core 4, i.e. the ratio of the weight of the SAP particles with respect to the total weight of the absorbent core 4 (which is the total weight of the fiber aggregate weight plus the SAP particle weight) is preferably no greater than 40 percent, for example.

The SAP particle weight ratio is calculated in the following manner. Specifically, 1 g each of the SAP sample and fiber sample is collected from the product to be measured (the absorbent core 4 is loosened, and the SAP and fibers are collected while using a magnifying glass or the like). Next, the collected SAP sample and fiber sample are placed in separate 250 mesh nylon bags to form test samples, and the water capacity of each is measured. The water capacity is calculated in the following manner. Specifically, the test sample is immersed in 500 ml of physiological saline for 30 minutes and then dewatered for 2 minutes at 150 G using a centrifugal separator, and the weight of the dewatered test sample is measured. The following formula is used to calculate the water capacity (g/g) of the SAP sample and the water capacity (g/g) of the fiber sample.

> Water capacity($g/g$) of the SAP or fiber sample=
> (weight of the test sample after dewatering−
> weight of nylon mesh−weight of the SAP or fiber
> sample before immersing−residual liquid weight
> of nylon mesh)/(weight of the SAP or fiber
> sample before immersing)

For this example, the weight of each of the SAP and fiber samples before immersing was 1 g.

Next, a 50 mm×50 mm absorbent core sample is prepared from the product to be measured (the size of the absorbent core sample may vary depending on the size of the product, but should be prepared as large as possible). The weight of the entire absorbent core sample T (g) is then measured.

The absorbent core sample is then placed in a 250 mesh nylon mesh bag to form a test sample and immersed for 30 minutes in 500 ml of physiological saline, after which it is dewatered for 10 minutes at 150 G using a centrifugal separator, and the weight of the dewatered test sample is measured and the water capacity of the absorbent core sample is determined.

If the SAP weight of the absorbent core sample is represented as S (g) and the fiber weight as P (g) (T=S+P), the following equation applies.

Water capacity of absorbent core sample(g)=
water capacity of SAP sample(g/g)×S(g)+water
capacity of fiber sample(g/g)×(T−S)(g)

The SAP weight S is calculated by the formula specified above. The following formula is then used to calculate the SAP particle weight ratio.

SAP particle weight ratio(%)=S/T

As shown in FIG. 1, the length of the front sheet 2 in the lengthwise direction is longer than the length of the absorbent core 4 in the lengthwise direction. As a result, the front sheet 2 is provided with extended sections 2E that extend outward in the lengthwise direction from both ends of the absorbent core 4 in the lengthwise direction. The length of each of the extended sections 2E in the lengthwise direction is preferably 25 mm or greater, for example.

At the intermediate section between the two extended sections 2E, as shown in FIG. 2, the front sheet 2 covers the skin side surface 4S of the absorbent core 4 while also being directly bonded to the skin side surface 4S. In other words, no separate sheet is provided between the front sheet 2 and absorbent core 4, and the fibers and/or SAP of the absorption core 4 are directly contactable with the front sheet 2. Also, the front sheet 2 covers both lateral edges 4L of the absorbent core 4 and covers up to the non-skin side surface 4NS of the absorbent core 4. Likewise, fibers and/or SAP of the absorption core 4 along the lateral edges 4L and at least in a portion of the non-skin side surface 4NS are directly contactable with the front sheet 2. In the first embodiment of the present invention, both lateral portions of the front sheet 2 are overlapped together at an overlapped section 2W, so that the front sheet 2 covers the entire non-skin side surface 4NS. In other words, the front sheet 2 is folded along folding lines parallel to the lengthwise direction L, and wrapped around (therefore surrounding) the absorbent core 4.

In this example, the skin side section 2S of the front sheet 2 and the skin side surface 4S of the absorbent core 4 are bonded together by a hot-melt adhesive 5S, and the non-skin side section 2NS of the front sheet 2 and the non-skin side surface 4NS of the absorbent core 4 are bonded together by a hot-melt adhesive 5NS. As a result, the liquid to be absorbed, that is inside the front sheet 2, can be rapidly transferred to the absorbent core 4.

The non-skin side section 2NS of the front sheet 2 is preferably also bonded together with the back sheet 3 by a hot-melt adhesive 6. Here, the hot-melt adhesive 6 is continuously applied in the lengthwise direction and transverse direction, so that the front sheet 2 is continuously connected (joined) to the back sheet 3 in the lengthwise direction and transverse direction.

At the extended sections 2E, as shown in FIG. 3, the skin side section 2S of the front sheet 2 is bonded, on its under side (i.e., the back side spunbond layer), together with the non-skin side section 2NS that overlaps the extended sections 2E, by a hot-melt adhesive 7. Here, the hot-melt adhesive 7 is continuously applied in the lengthwise direction and transverse direction, so that the skin side section 2S is continuously connected to the non-skin side section 2NS in the lengthwise direction and transverse direction.

Figure 4:
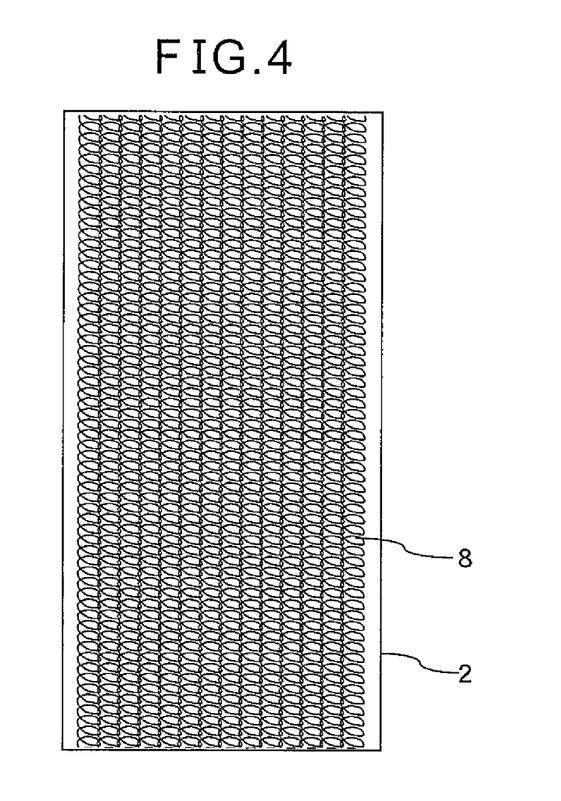
FIG. 4 is a schematic view of an adhesive application pattern.

FIG. 4 shows an example of the pattern of a hot-melt adhesive 8 applied to the front sheet 2. In this example, the hot-melt adhesive 8 is applied in the form of a plurality of helices extending parallel to each other in the lengthwise direction, with each helical adhesive 8 partially overlapping its adjacent helical adhesives 8, as best seen in the magnified view of FIG. 5. The adhesive 8 is thus continuously applied in both the lengthwise direction and the transverse direction.

Figure 5:
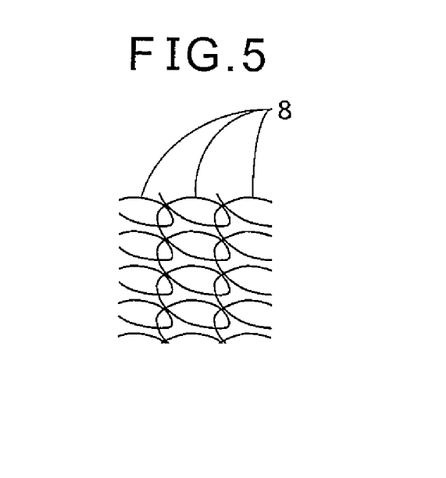
FIG. 5 is a magnified view of the adhesive application pattern of FIG. 4.

When the front sheet 2 with the adhesive 8 applied thereon is wrapped around the absorption core 4, the adhesive 8 defines the adhesives 5S, 5NS and 7 described above.

As a result, the absorbent core 4, and especially the SAP particles, are securely enveloped inside the interior body 1, so that leakage of the SAP particles out from the interior body 1 is suppressed.

That is, the front sheet 2 also functions as a core wrap surrounding the absorbent core 4. Therefore, the core wrap and second sheet can be eliminated, thus allowing the production cost of the diaper to be greatly reduced.

In this case, the front sheet 2 has sufficient tensile strength in both the lengthwise direction and the transverse direction, both when dry and when wet. Consequently, leaking out of the absorbent core 4, and especially the SAP particles, can be reliably suppressed even with elimination of the core wrap.

In addition, since the front sheet 2 includes a melt blown layer, leaking out of the SAP particles is even more reliably suppressed. At the same time, the spunbond layer on the front side of the front sheet 2 comes in contact with the skin of the wearer in use, and as a result, a satisfactory feel on the skin is obtained. Handling is also facilitated since the front sheet 2 comprises a spunbond/melt blown/spunbond three-layer structure.

Furthermore, since the spunbond layer on the front side of the front sheet 2 is pattern embossed, high-compression regions, in which the fibers are contact bonded together, and low-compression regions, in which the fibers are essentially not contact bonded together, are formed in said spunbond layer on the front side. Since the degree of freedom of the fibers is relatively high in the low-compression regions, liquids to be absorbed, such as urine, can be easily drawn into the front sheet 2.

On the other hand, since the spunbond layer on the back side of the front sheet 2 is flat embossed, the spunbond layer on the back side is essentially evenly compressed in overall. The strength of the spunbond layer on the back side (which comes in direct contact with the absorption core 4) is thereby increased, and therefore damage to the front sheet 2 by the absorbent core 4 and especially the SAP particles, is suppressed. Also, the high fiber density of the flat embossed spunbond layer on the back side suppresses the SAP particles from passing through the front sheet 2 and leaking out from the absorbent core 4.

Moreover, because the fiber density of the spunbond layer on the back side is higher than that of the spunbond layer on the front side, liquid diffusion from the spunbond layer on the front side to the spunbond layer on the back side is accelerated. In addition, since the two spunbond layers each have fiber orientation in the lengthwise direction, liquid diffusion in the lengthwise direction is accelerated.

A front sheet 2 of an exemplary embodiment of the present invention (spunbond layer: 4 g/m$^2$ on the front side, spunbond layer: 4 g/m$^2$ on the back side, melt blown layer: 2 g/m$^2$ between the two spunbond layers) was subjected to a Klemm water absorption test, through which it was found that the liquid diffusibility in the lengthwise direction was 20 to 30 mm while the liquid diffusibility in the transverse direction was 5 to 15 mm. Thus, the front sheet 2 has high liquid diffusibility even though it is a simple sheet.

It should be noted that an ordinary top sheet (polyethylene/polypropylene fiber spunbond, 20 g/m$^2$) to be contacted with a wearer's skin has the liquid diffusibility in the lengthwise direction was 10 to 15 mm and the liquid diffusibility in the transverse direction was 5 to 15 mm. In contrast, the liquid diffusibility of an ordinary tissue sheet used as the sheet surrounding an absorbent core is 25 to 35 mm in both the lengthwise direction and the transverse direction.

Furthermore, leaking out of the SAP particles can be suppressed with a SAP particle weight ratio of no greater than 40 percent. With a higher SAP particle weight ratios, the fiber aggregates may not be able to contain SAP particles inside, and the front sheet 2 may be damaged by movement of the wearer, increasing the possibility of leaking out of the SAP particles.

This has been confirmed experimentally. The experiment was conducted in the following manner. Specifically, several absorbers, each of which is defined as an absorbent core 4 surrounded by a front sheet 2, were prepared with different SAP particle weight ratios. The SAP particle weight ratio of the absorbers were 20%, 25%, 30%, 35%, 40%, 45%, 50%, 55% and 60%. The absorbent cores, absorbent core wrap sheets and front sheets were removed from commercial diapers (trade name: MoonyMan, L-size), and the absorbers were attached to the remainders of the commercial diapers to prepare diaper samples.

Five L-size users were first asked to wear black fabric underpants. This was to allow leaked off SAP particles to be easily confirmed, without adhesion of the leaked SAP particles onto the skin of the user. The users were then asked to wear the prepared diaper samples. After this, the users were allowed free activity for 30 minutes, including movements of sleeping posture, standing, running, walking and sitting. Next, 80 ml of physiological saline was absorbed into the absorber of each diaper sample, and the users were allowed activity for 30 minutes in the same manner. The presence or absence of SAP particles on the surface of the diaper and the fabric underpants surfaces was then confirmed.

No leaking out of SAP particles occurred with a SAP particle weight ratios of up to 40%. With a SAP particle weight ratio of 45%, the SAP leaked out in 2 of the 5 users.

Figure 6:
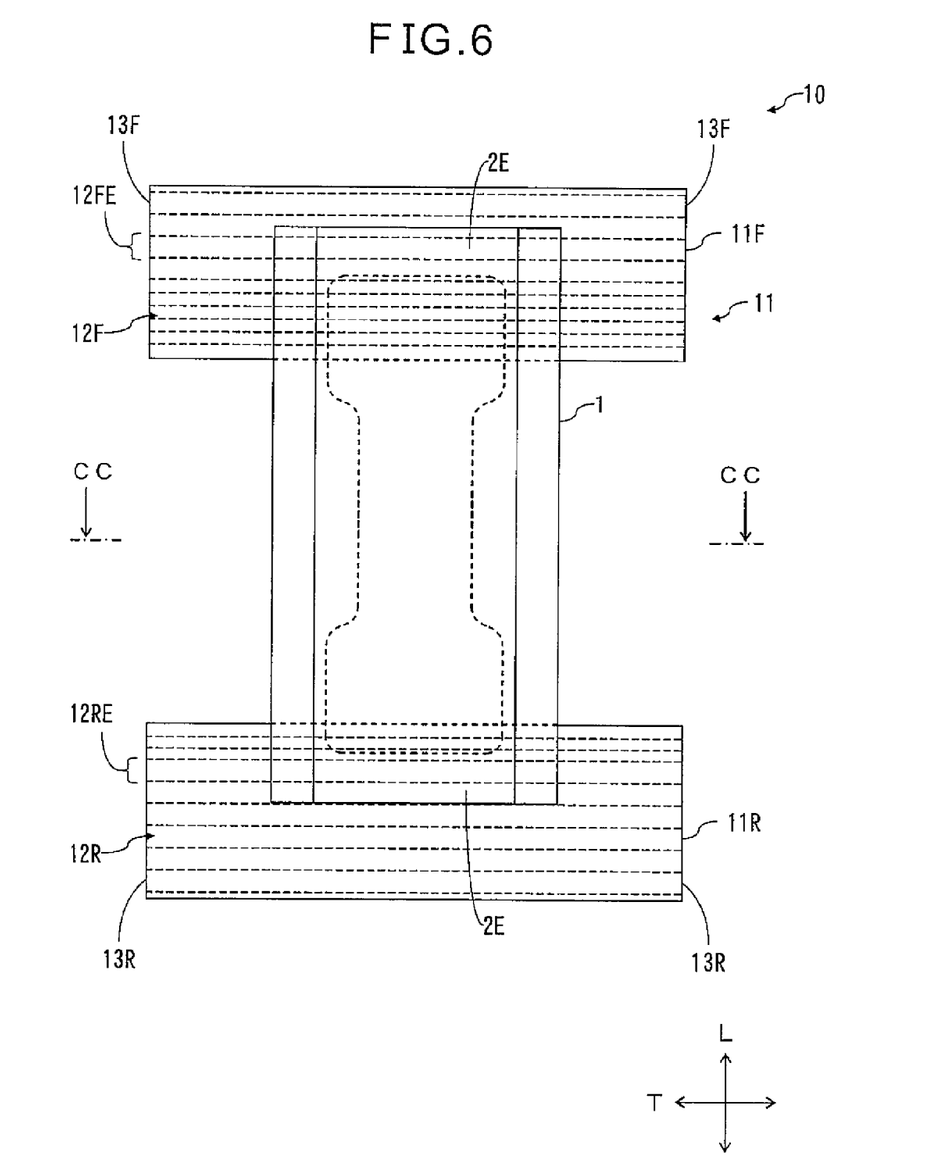
FIG. 6 is a plan view of a diaper, in accordance with a first embodiment of the present invention.
Figure 7:
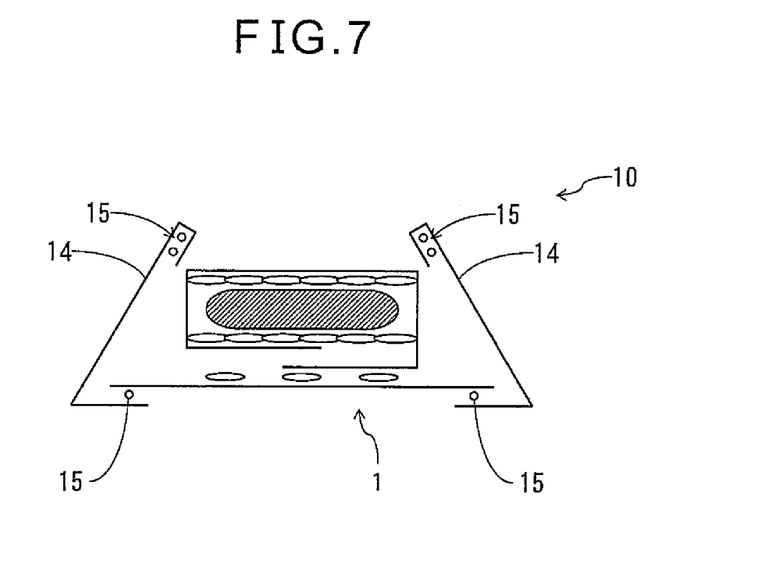
FIG. 7 is a schematic cross-sectional view of FIG. 6 along line CC-CC.

The diaper 10 shown in FIG. 6 and FIG. 7 was formed by combining the interior body 1 described above with an exterior body 11. In this embodiment, the exterior body 11 comprises an abdominal side section 11F situated on the front side or abdominal side of the wearer, and a dorsal side section 11R situated on the rear side or dorsal side of the wearer, the abdominal side section 11F and dorsal side section 11R being mutually separate. However, the abdominal side section and dorsal side section may also be integrally formed.

The back sheet 3 of the interior body 1 is bonded to the abdominal side section 11F and the dorsal side section 11R of the exterior body 11 at its ends in the lengthwise direction. The flank section 13F of the abdominal side section 11F and the flank section 13R of the dorsal side section 11R may be bonded together, thereby forming a "pants diaper".

The abdominal side section 11F and the dorsal side section 11R each have a plurality of elastic members 12F and 12R extending parallel to each other in the transverse direction, and integrated in a stretched state.

Elastic member parts 12FE, 12RE of the elastic members 12F, 12R overlap the extended sections 2E of the interior body 1. As a result, the extended sections 2E contract in the transverse direction during wear, so that leaking out of the SAP particles through the extended sections 2E is further suppressed.

In addition, there is no sheet covering the extended sections 2E, and therefore the extended sections 2E can directly contact the skin of the wearer. It is thus possible to increase the absorption area of the diaper.

In FIG. 7, 14 denotes anti-leakage members formed on both sides of the interior body 1, and 15 denotes elastic members integrated into the anti-leakage members 14. The anti-leakage members may be omitted, in some embodiments.

Figure 8:
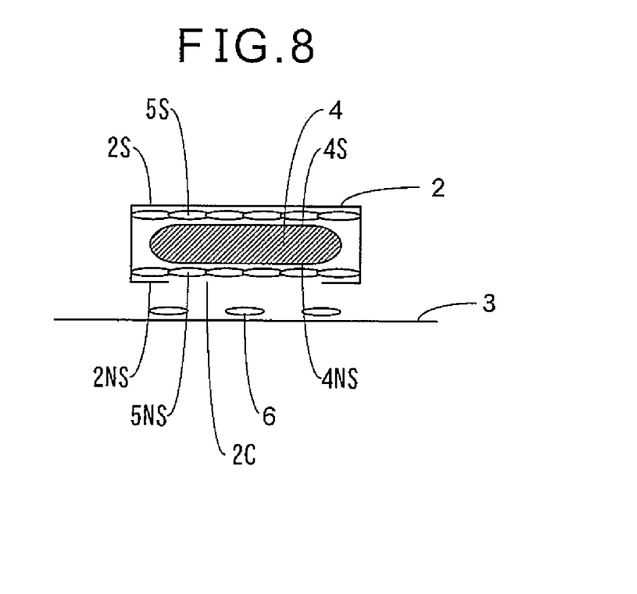
FIG. 8 is a schematic cross-sectional view similar to FIG. 2, illustrating an interior body in accordance with a second embodiment of the present invention.
Figure 9:
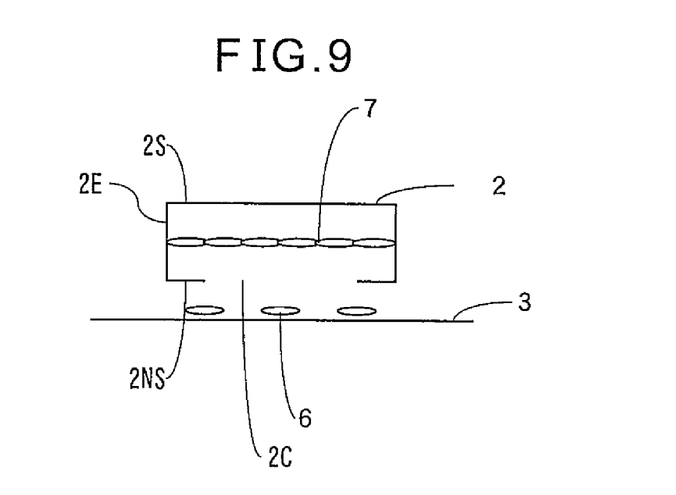
FIG. 9 is a schematic cross-sectional view similar to FIG. 3, illustrating the interior body in accordance with the second embodiment of the present invention.

In the second embodiment of the present invention exemplarily illustrated in FIG. 8 and FIG. 9, the front sheet 2 only partially covers the non-skin side surface 4NS of the absorbent core 4, i.e., it does not cover the entirety of the non-skin side surface 4NS. In other words, no separate sheet is situated between the non-skin side surface 4NS of the absorbent core 4 and the back sheet 3, and therefore the non-skin side surface 4NS of the absorbent core 4 is directly bonded to the back sheet 3. In this case, a clearance 2C is formed where the front sheet 2 does not cover the absorbent core 4. Also, as shown in FIG. 9, the skin side section 2S of the front sheet 2 on the extended sections 2E is bonded with the non-skin side section 2NS and the back sheet 3 which overlap the skin side section 2S, by hot-melt adhesives 6,7. This allows reduction in the amount of material necessary to form the front sheet 2.

Figure 10:
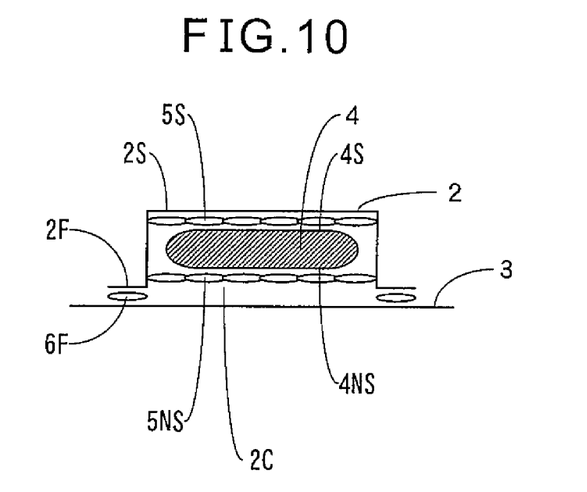
FIG. 10 is a schematic cross-sectional view similar to FIG. 2, illustrating an interior body in accordance with a third embodiment of the present invention.
Figure 11:
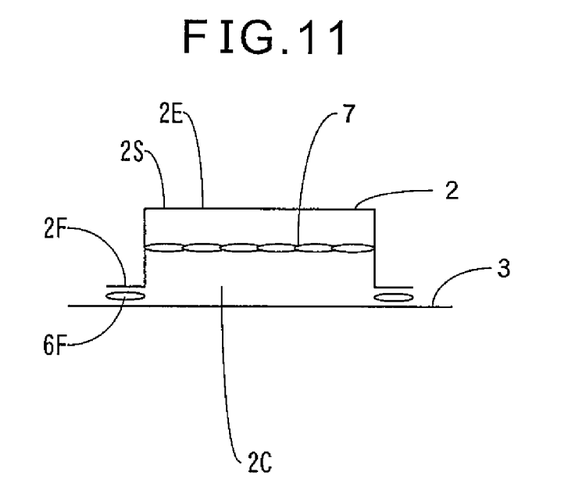
FIG. 11 is a schematic cross-sectional view similar to FIG. 3, illustrating the interior body in accordance with the third embodiment of the present invention.

In the third embodiment of the present invention exemplarily illustrated in FIG. 10 and FIG. 11, the front sheet 2 does not cover any part of the non-skin side surface 4NS of the absorbent core 4, and it has instead a pair of flange sections 2F that protrude outward in the transverse direction. The flange sections 2F are bonded to the back sheet 3 by a hot-melt adhesive 6F. In this case, the flange sections 2F are continuously bonded to the back sheet 3 in the lengthwise direction and the transverse direction. Also, as shown in FIG. 11, the skin side section 2S of the front sheet 2 on the extended sections 2E is bonded with the back sheet 3 which overlaps the skin side section 2S, by a hot-melt adhesive 7. A clearance 2C is formed in this embodiment as well. The non-skin side surface 4NS of the absorption core 4 is directly bonded to the back sheet 3 in this clearance 2C by the hot-melt adhesive 5NS. According to the third embodiment, the leakage of the absorbent core 4 and especially of the SAP particles out from the interior body 1 is suppressed.

Figure 12:
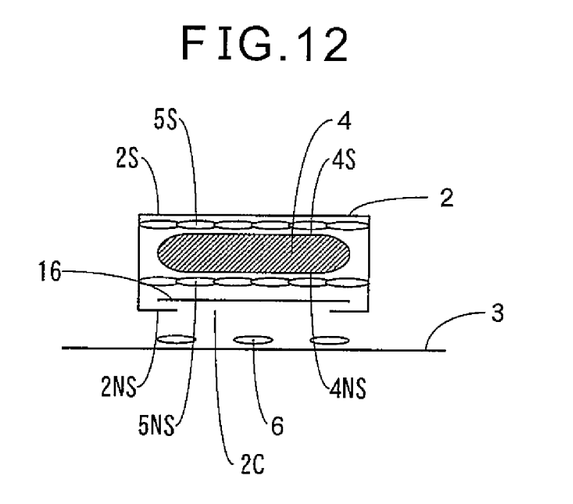
FIG. 12 is a schematic cross-sectional view similar to FIG. 2, illustrating an interior body in accordance with a fourth embodiment of the present invention.
Figure 13:
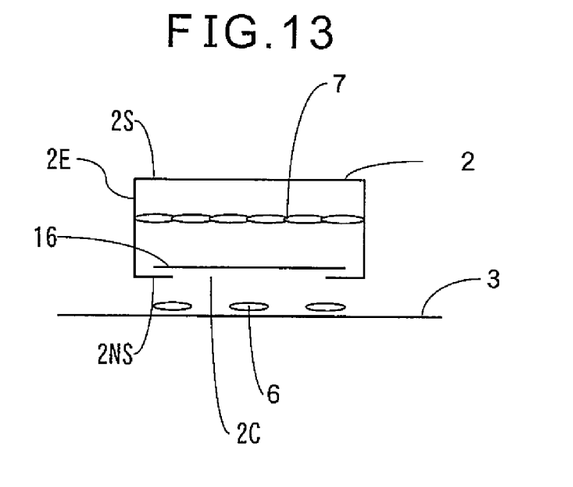
FIG. 13 is a schematic cross-sectional view similar to FIG. 3, illustrating the interior body in accordance with the fourth embodiment of the present invention.

The fourth embodiment of the present invention exemplarily illustrated in FIG. 12 and FIG. 13 corresponds to the second embodiment illustrated in FIG. 8 and FIG. 9, except that an additional sheet 16 covering the non-skin side surface 4NS of the absorbent core 4 is situated in the clearance 2C. The additional sheet 16 is bonded to the non-skin side surface 4NS of the absorbent core 4 by a hot-melt adhesive 5NS, and is bonded to the back sheet 3 by a hot-melt adhesive 6. Also, as shown in FIG. 13, the skin side section 2S of the front sheet 2 on the extended sections 2E is bonded with the additional sheet 16 which overlaps the skin side section 2S, by a hot-melt adhesive 7. As a result, damage to the back sheet 3 by the SAP particles can thus be suppressed. When the back sheet 3 is damaged by the SAP particles, the SAP particles can potentially leak out through the back sheet 3.

Figure 14:
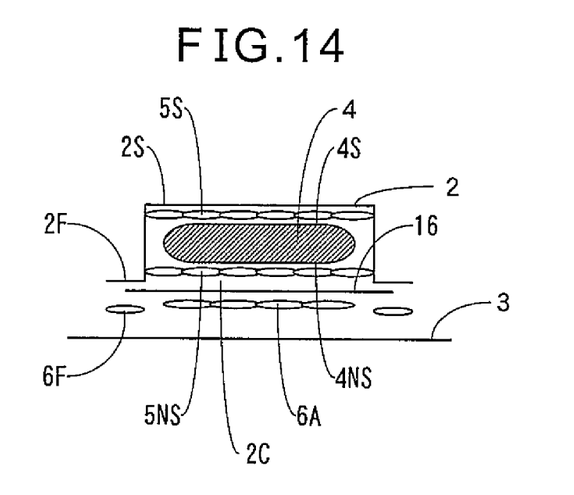
FIG. 14 is a schematic cross-sectional view similar to FIG. 2, illustrating an interior body in accordance with a fifth embodiment of the present invention.
Figure 15:
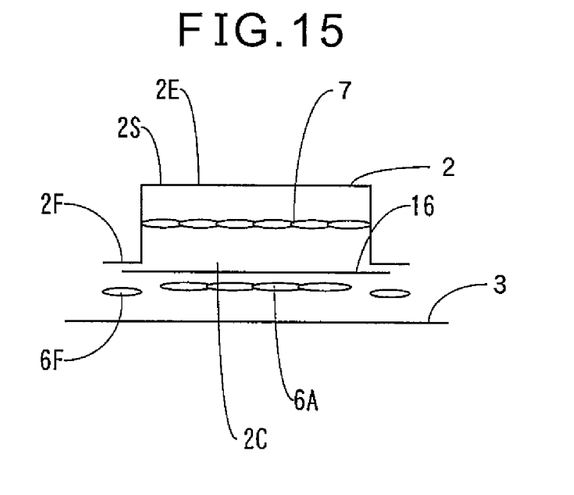
FIG. 15 is a schematic cross-sectional view similar to FIG. 3, illustrating the interior body in accordance with the fifth embodiment of the present invention.

The fifth embodiment of the present invention exemplarily illustrated in FIG. 14 and FIG. 15 corresponds to the third embodiment illustrated in FIG. 10 and FIG. 11, except that an additional sheet 16 covering the non-skin side surface 4NS of the absorbent core 4 is situated in the clearance 2C. The additional sheet 16 is bonded to the non-skin side surface 4NS of the absorbent core 4 by a hot-melt adhesive 5NS, and is bonded to the back sheet 3 by a hot-melt adhesive 6A. Also, as shown in FIG. 15, the skin side section 2S of the front sheet 2 on the extended sections 2E is bonded with the additional sheet 16 which overlaps the skin side section 2S, by a hot-melt adhesive 7. As a result, damage to the back sheet 3 by the SAP particles can be suppressed.

Figure 16:
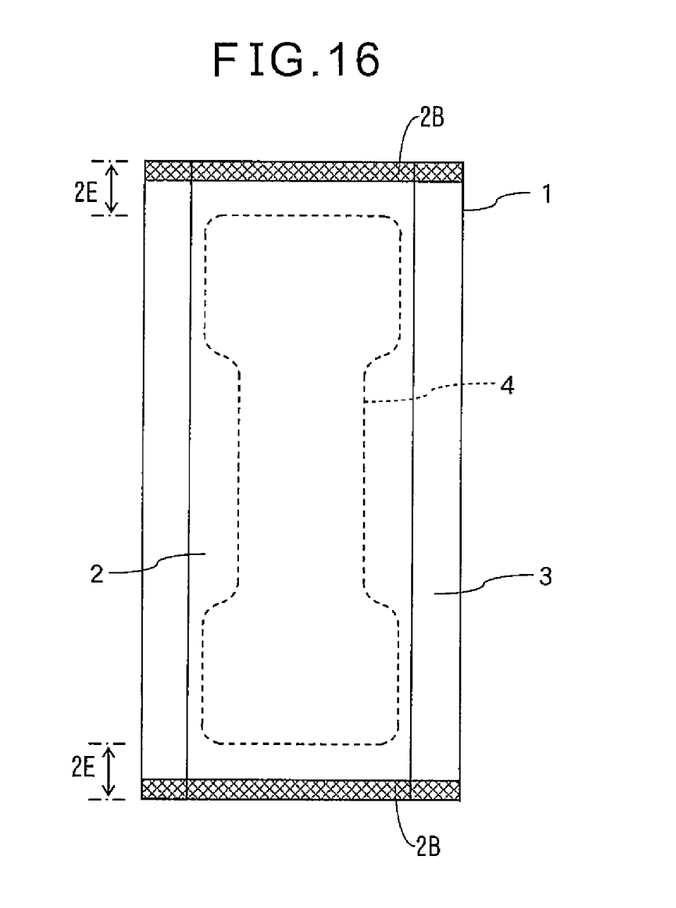
FIG. 16 is a plan view of an interior body, illustrating an interior body in accordance with a sixth embodiment of the present invention.

In the sixth embodiment of the present invention exemplarily illustrated in FIG. 16, the extended sections 2E of the front sheet 2 have embossed regions 2B in which the extended sections 2E are embossed together with the front sheet 2 (including the extended sections 2E) that overlaps with the extended sections 2E, or together with the back sheet 3 that overlaps with the extended sections 2E. This can reliably suppress leaking out of the SAP particles through the extended sections 2E.

In some embodiments, the front sheet 2 may consist of a single sheet which is a laminated sheet of spunbond layers on the front side and back side, and two melt blown layers between the spunbond layers. This will allow leaking out of the SAP particles to be even more reliably suppressed.

This application claims the benefit of Japanese Application No. 2010-223096 the entire disclosure of which is incorporated by reference herein.

The present invention is also defined by the following non-limiting features Ea to Eq, E1 to E13, and U1 to U15, which are not specific to the detailed embodiments described above:

Ea The front sheet is formed by laminating the front side and back side spunbond layers and the melt blown layer and then pattern embossing the spunbond layer on the front side while flat embossing the spunbond layer on the back side.

Eb The liquid diffusibility of the front sheet is at least 20 mm by a Klemm water absorption test.

Ec The weight ratio of the super-absorbent polymer particles in the absorbent core is no greater than 40 percent.

Ed The tensile strength of the front sheet in each of the lengthwise direction and the transverse direction is least 4.0 N/25 mm, both when dry and when wet.

Ee The front sheet covers both lateral edges of the absorbent core and extends to the non-skin side surface of the absorbent core.

Ef The front sheet covers the entire non-skin side surface of the absorbent core.

Eg The front sheet partially covers the non-skin side surface of the absorbent core.

Eh The front sheet does not cover the non-skin side surface of the absorbent core but has a pair of flange sections extending outwards in the transverse direction, said flange sections being bonded to the back sheet.

Ei The non-skin side surface of the absorbent core is directly bonded to the back sheet.

Ej An additional sheet is provided, that covers the non-skin side surface of the absorbent core between the absorbent core and the back sheet. The additional sheet is provided only on the non-skin side surface of the absorbent core and does not cover the skin side surface of the absorbent core.

Ek The extended sections of the front sheet are embossed together with the front sheet or back sheet which overlaps with the extended sections.

El The front sheet consists of a simple sheet including two spunbond layers and two melt blown layers between the spunbond layers.

Em The absorbent article does not include a core wrap or a secondary sheet.

En There is no sheet covering the extended sections.

Eo The extended sections consist only of the front sheet.

Ep The extended sections consist of the front sheet and the back sheet.

Eq The extended sections consist of the front sheet and the back sheet, and an additional sheet which is provided on the non-skin side surface of the absorbent core.

Er An absorbent chassis consisting of a liquid-permeable front sheet, or top sheet; a liquid-impermeable back sheet; and a liquid-retaining absorbent core; in which the front sheet consists of a single sheet comprising spunbond layers on the front side and back side and a melt blown layer between the spunbond layers; the absorbent core consists of fiber aggregates and super-absorbent polymer particles; the front sheet covers the skin side surface of the absorbent core and is directly bonded thereto; the length of the front sheet, and optionally the back sheet and/or another sheet which is an optional additional sheet provided only on the non-skin side surface of the absorbent core, in the lengthwise direction is longer than the length of the absorbent core in the lengthwise direction so as to provide extended sections which extend outward from both ends of the absorbent core in the lengthwise direction; the components of said extended sections are continuously joined together in the transverse direction; and the extended sections are adapted for contacting the skin of a wearer.

E1 An absorbent article comprising:
  a liquid-permeable front sheet, or top sheet;
  a liquid-impermeable back sheet; and
  a liquid-retaining absorbent core;
wherein:
  the front sheet consists of a single sheet comprising spunbond layers on the front side and back side and a melt blown layer between the spunbond layers;
  the absorbent core consists of fiber aggregates and super-absorbent polymer particles;
  the front sheet covers the skin side surface of the absorbent core and is directly bonded thereto;
  the length of the front sheet, and optionally the back sheet and/or another sheet which is an optional additional sheet provided only on the non-skin side surface of the absorbent core, in the lengthwise direction is longer than the length of the absorbent core in the lengthwise direction so as to provide extended sections which extend outward from both ends of the absorbent core in the lengthwise direction;
  the components of said extended sections being continuously joined together in the transverse direction; and
  the extended sections being adapted for contacting the skin of a wearer.

E2 An absorbent article as in E1, wherein:
  the front sheet is formed by laminating the front side and back side spunbond layers and the melt blown layer and then pattern embossing the spunbond layer on the front side while flat embossing the spunbond layer on the back side.

E3 An absorbent article as in E1 or E2, wherein the liquid diffusibility of the front sheet is at least 20 mm by a Klemm water absorption test.

E4 An absorbent article as in any one of E1 to E3, wherein the weight ratio of the super-absorbent polymer particles in the absorbent core is no greater than 40 percent.

E5 An absorbent article as in any one of E1 to E4, wherein the tensile strength of the front sheet in each of the lengthwise direction and the transverse direction is least 4.0 N/25 mm, both when dry and when wet.

E6 An absorbent article as in any one of E1 to E5, wherein the front sheet covers both lateral edges of the absorbent core and extends to the non-skin side surface of the absorbent core.

E7 An absorbent article as in any one of E1 to E6, wherein the front sheet covers the skin side surface of the absorbent core and is directly bonded thereto; the front sheet covers both lateral edges of the absorbent core and extends to the non-skin side surface of the absorbent core; and the front sheet covers the entire non-skin side surface of the absorbent core.

E8 An absorbent article as in any one of E1 to E6, wherein the front sheet covers the skin side surface of the absorbent core and is directly bonded thereto; the front sheet covers both lateral edges of the absorbent core and extends to the non-skin side surface of the absorbent core; and the front sheet partially covers the non-skin side surface of the absorbent core.

E9 An absorbent article as in any one of E1 to E6, wherein the front sheet covers the skin side surface of the absorbent core and is directly bonded thereto; the front sheet covers both lateral edges of the absorbent core and extends to the non-skin side surface of the absorbent core; and the front sheet has a pair of flange sections extending outwards in the transverse direction, said flange sections being bonded to the back sheet.

E10 An absorbent article as in any one of E1 to E6 and E8 to E9, wherein the non-skin side surface of the absorbent core is directly bonded to the back sheet.

E11 An absorbent article as in any one of E1 to E10, further comprising an additional sheet that covers the non-skin side surface of the absorbent core between the absorbent core and the back sheet.

E12 An absorbent article as in any one of E1 to E11, wherein the extended sections of the front sheet are embossed together with the front sheet or back sheet which overlaps with the extended sections.

E13 An absorbent article as in any one of E1 to E12, wherein the front sheet consists of a simple sheet including two spunbond layers and two melt blown layers between the spunbond layers.

U1 An absorptive article, comprising a liquid-permeable front sheet, a liquid-impermeable back sheet and a liquid-retaining absorption core, wherein
    the front sheet consists of a single sheet comprising spunbond layers on a front side and a back side, respectively, and a melt blown layer between the spunbond layers,
    the absorption core consists of fiber aggregates and super-absorbent polymer particles,
    the front sheet covers a skin side surface of the absorption core while being directly bonded to the skin side surface,
    a length of the front sheet in a lengthwise direction of the absorptive article is longer than a length of the absorption core in the lengthwise direction so that the front sheet has extended sections which extend outward in the lengthwise direction from both ends in the lengthwise direction of the absorption core, the extended sections being each continuously connected in a transverse direction of the absorptive article with the front sheet or back sheet which overlaps the extended section, and
    the extended sections are directly contactable with the skin of a wearer.

U2 An absorptive article according to U1, wherein:
    the single sheet of the front sheet is a laminated sheet formed by stacking the spunbond layers on the front side and back side with the melt blown layer in between, and then pattern embossing the spunbond layer on the front side while flat embossing the spunbond layer on the back side,
    a liquid diffusibility of the front sheet in the lengthwise direction is at least 20 mm by a Klemm water absorption test, and
    a weight ratio of the super-absorbent polymer particles in the absorption core is no greater than 40 percent.

U3 An absorptive article according to U1 or U2, wherein both a tensile strength in the lengthwise direction and a tensile strength in the transverse direction of the front sheet are at least 4.0 N/25 mm, both when dry and when wet.

U4 An absorptive article according to any one of U1 to U3, wherein the front sheet covers both lateral edges of the absorption core and extends to a non-skin side surface of the absorption core.

U5 An absorptive article according to U4, wherein the front sheet covers the entire non-skin side surface of the absorption core.

U6 An absorptive article according to any one of U1 to U4, wherein the non-skin side surface of the absorption core is directly bonded to the back sheet.

U7 An absorptive article according to any one of U1 to U4, further comprising an additional sheet that covers the non-skin side surface of the absorption core and is disposed between the absorption core and the back sheet.

U8 An absorptive article according to any one of U1 to U7, wherein the extended sections of the front sheet are embossed together with the front sheet or back sheet which overlaps the extended sections.

U9 An absorptive article according to any one of U1 to U8, wherein the single sheet includes two spunbond layers disposed between and laminated to the spunbond layers.

U10 An absorptive article according to any one of U1 to U3, wherein the front sheet does not cover a non-skin side surface of the absorption core, and includes a pair of flange sections that protrude outward in the transverse direction from the absorption core and are bonded to the back sheet.

U11 An absorptive article according to any one of U1 to U10, wherein
    the spunbond layer on the front side is directly contactable with the skin of the wearer; and
    the spunbond layer on the back side is directly contactable with at least one of the fiber aggregates or super-absorbent polymer particles of the absorption core.

U12 An absorptive article according to any one of U1 to U11, wherein
    a fiber density of the spunbond layer on the back side is higher than that of the spunbond layer on the front side.

U13 An absorptive article according to any one of U1 to U12, wherein
    both the spunbond layer on the back side and the spunbond layer on the front side have fiber orientations in the lengthwise direction.

U14 An absorptive article, comprising a liquid-permeable front sheet, a liquid-impermeable back sheet and a liquid-retaining absorption core, wherein
    the front sheet consists of a single, laminated sheet of spunbond layers on a front side and a back side, respectively, and a melt blown layer between the spunbond layers,
    the absorption core contains fiber aggregates and super-absorbent polymer particles,
    the front sheet covers a skin side surface of the absorption core while being directly bonded to the skin side surface,
    the spunbond layer on the front side is directly contactable with the skin of the wearer, and the spunbond layer on the back side is directly contactable with at least one of the fiber aggregates or super-absorbent polymer particles of the absorption core.

U15 An absorptive article, comprising a liquid-permeable front sheet, a liquid-impermeable back sheet and a liquid-retaining absorption core, wherein
    the front sheet consists of a single, laminated sheet of spunbond layers on a front side and a back side, respectively, and a melt blown layer between the spunbond layers,
    the absorption core contains fiber aggregates and super-absorbent polymer particles, the front sheet covers a skin side surface of the absorption core while being directly bonded to the skin side surface, the spunbond layer on the front side is directly contactable with the skin of the wearer, and the spunbond layer on the back side is directly contactable with at least one of the fiber aggregates or super-absorbent polymer particles of the absorption core, a liquid diffusibility of the front sheet in a lengthwise direction of the absorptive article is at least 20 mm by a Klemm water absorption test, a weight ratio of the super-absorbent polymer particles in the absorption core is no greater than 40 percent, and both tensile strengths of the front sheet in the lengthwise direction and in a transverse direction of the absorptive article are at least 4.0 N/25 mm, both when the front sheet is dry and wet.

C1 An absorbent article comprising a liquid-permeable front sheet, a liquid-impermeable back sheet and a liquid-retaining absorbent core, wherein the front sheet consists of a single sheet comprising spunbond layers on the front side and back side and a melt blown layer between the spunbond layers, the absorbent core consists of fiber aggregates and super-absorbent polymer particles, the front sheet covers the skin side surface of the absorbent core while being directly bonded to the skin side surface, the length of the front sheet in the lengthwise direction is longer than the length of the absorbent core in the lengthwise direction so that the front sheet is provided with extended sections which extend outward in the lengthwise direction from both ends in the lengthwise direction of the absorbent core, the extended sections being each continuously connected in the transverse direction with the front sheet which overlaps with the extended section, or with the back sheet which overlaps with the extended section, and the extended sections can be contacted with the skin of a wearer.

C2 An absorbent article according to C1, wherein:

the front sheet is formed by laminating spunbond layers on the front side and back side and the melt blown layer and then pattern embossing the spunbond layer on the front side while flat embossing the spunbond layer on the back side, the liquid diffusibility of the front sheet is at least 20 mm by a Klemm water absorption test, and the weight ratio of the super-absorbent polymer particles in the absorbent core is no greater than 40 percent.

C3 An absorbent article according to C1 or C2, wherein both the tensile strength in the lengthwise direction and the tensile strength in the transverse direction of the front sheet are at least 4.0 N/25 mm, both when dry and when wet.

C4 An absorbent article according to any one of C1 to C3, wherein the front sheet covers both lateral edges of the absorbent core and extends to the non-skin side surface of the absorbent core.

C5 An absorbent article according to C4, wherein the front sheet covers the entire non-skin side surface of the absorbent core.

C5' An absorbent article according to C5, wherein the front sheet is directly bonded to the non-skin side surface of the absorbent core.

C5" An absorbent article according to C4, wherein the front sheet covers the partial non-skin side surface of the absorbent core.

C5'" An absorbent article according to C4, wherein the front sheet exposes the entire non-skin side surface of the absorbent core, and the front sheet has a pair of flange sections of the front sheet that protrude outward in the transverse direction and are bonded to the back sheet.

C6 An absorbent article according to any one of C1 to C4, wherein the non-skin side surface of the absorbent core is directly bonded to the back sheet.

C7 An absorbent article according to any one of C1 to C4, further comprising an additional sheet that covers the non-skin side surface of the absorbent core between the absorbent core and the back sheet.

C8 An absorbent article according to any one of C1 to C7, wherein the extended sections of the front sheet are embossed together with the front sheet which overlaps with the extended sections, or together with the back sheet which overlaps with the extended sections.

C9 An absorbent article according to any one of C1 to C8, wherein the front sheet consists of a simple sheet including two spunbond layers and two melt blown layers between the spunbond layers.

C10 An absorbent article according to C1, wherein the extended sections of the front sheet have embossed regions in which the extended sections are embossed or the extended sections are embossed together with the back sheet that overlaps with the extended sections.

REFERENCE SIGN LIST

1 Interior body
2 Front sheet
2B Embossed regions
2C Clearance
2E Extended sections
2F Flange sections
2S Skin side section
2NS Non-skin side section
2W Overlapped section
3 Back sheet
4 Absorbent core
4L Lateral edges
4S Skin side surface
4NS Non-skin side surface
5S, 5NS Hot melt adhesive
6, 6A, 6F Hot melt adhesive
7 Hot melt adhesive
8 Hot melt adhesive
10 Diaper
11 Exterior body
11F Abdominal side section
11R Dorsal side section
12F, 12R Elastic members
12FE, 12RE Elastic member parts
13F, 13R Flank sections
14 Anti-leakage member
15 Elastic members integrated into 14
16 Additional sheet

The invention claimed is:

1. An absorbent article comprising a liquid-permeable front sheet, a liquid-impermeable back sheet and a liquid-retaining absorbent core, wherein the front sheet consists of a single laminated sheet comprising spunbond layers on front and back sides and at least one melt blown layer between the spunbond layers, wherein the spunbond layer on the front side has a pattern embossed surface, and the spunbond layer on the back side has a flat embossed surface, the absorbent core consists of fiber aggregates and super-absorbent polymer particles, the front sheet covers a skin side surface of the absorbent core while being directly bonded to the skin side surface, the length of the front sheet in a lengthwise direction of the absorbent article is longer than the length of the absorbent core in the lengthwise direction so that the front sheet is provided with extended sections which extend outward in the lengthwise direction from both ends in the lengthwise direction of the absorbent core, the extended sections being each continuously connected in a transverse direction of the absorbent article with the front sheet or back sheet which overlaps with the extended section, the extended sections are adapted to contact the skin of a wearer, the spunbond layer on the front side is directly contactable with the skin of the wearer, the spunbond layer on the back side is in direct contact with at least one of the fiber aggregates or super-absorbent polymer particles on the skin side surface of the absorbent core, and a fiber density of the spunbond layer on the back side is higher than that of the spunbond layer on the front side.

2. An absorbent article according to claim 1, wherein:

the liquid diffusibility of the front sheet is at least 20 mm by a Klemm water absorption test, and the weight ratio of the super-absorbent polymer particles in the absorbent core is no greater than 40 percent.

3. An absorbent article according to claim 1, wherein both the tensile strength in the lengthwise direction and the tensile strength in the transverse direction of the front sheet are at least 4.0 N/25 mm, both when dry and when wet.

4. An absorbent article according to claim 1, wherein the front sheet covers both lateral edges of the absorbent core and extends to a non-skin side surface of the absorbent core.

5. An absorbent article according to claim 4, wherein the front sheet covers the entire non-skin side surface of the absorbent core.

6. An absorbent article according to claim 1, wherein a non-skin side surface of the absorbent core is directly bonded to the back sheet.

7. An absorbent article according to claim 1, further comprising an additional sheet that covers a non-skin side surface of the absorbent core and is arranged between the absorbent core and the back sheet.

8. An absorbent article according to claim 1, wherein the extended sections of the front sheet are embossed together with the front sheet or back sheet which overlaps with the extended sections.

9. An absorbent article according to claim 1, wherein the single laminated sheet includes said two spunbond layers and two melt blown layers between the spunbond layers.

10. An absorptive article according to claim 1, wherein
both the spunbond layer on the back side and the spunbond layer on the front side have fiber orientations in the lengthwise direction.

11. An absorptive article according to claim 1, wherein
the spunbond layer on the front side includes high-compression regions, in which fibers are contact-bonded together, and low-compression regions, in which the fibers are essentially not contact-bonded together, and
the spunbond layer on the back side is essentially evenly compressed in overall.

\* \* \* \* \*